US00PP18435P2

(12) United States Plant Patent
McDonald

(10) Patent No.: US PP18,435 P2
(45) Date of Patent: Jan. 15, 2008

(54) ***ARGYRANTHEMUM* PLANT NAMED 'SUPA742'**

(50) Latin Name: *Argyranthemum frutescens*
Varietal Denomination: Supa742

(75) Inventor: Daniel Bede McDonald, Seven Hills (AU)

(73) Assignee: NuFlora Intl. Pty Ltd., Macquarie Fields, NSW (AU)

( * ) Notice: Subject to any disclaimer, the term of this patent is extended or adjusted under 35 U.S.C. 154(b) by 0 days.

(21) Appl. No.: 11/520,896

(22) Filed: Sep. 14, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—Annette Para
(74) *Attorney, Agent, or Firm*—C A. Whealy

(57) ABSTRACT

A new and distinct cultivar of *Argyranthemum* plant named 'Supa742', characterized by its compact, uniform, outwardly spreading and mounded plant habit; freely branching growth habit; freely flowering habit; daisy-type inflorescences with red purple-colored ray florets; and good garden performance.

1 Drawing Sheet

Botanical designation: *Argyranthemum frutescens.*
Cultivar denomination: 'Supa742'.

BACKGROUND OF THE INVENTION

The present invention relates to a new and distinct cultivar of *Argyranthemum* plant, botanically known as *Argyranthemum frutescens* and hereinafter referred to by the name 'Supa742'.

The objective of the breeding program is to create new compact *Argyranthemum* cultivars with desirable and unique inflorescence form and floret colors.

The new *Argyranthemum* originated from a cross-pollination in Cobbitty, New South Wales, Australia in September, 2002, of a proprietary selection of *Argyranthemum frutescens* identified as code number X01.329.2, not patented, as the female, or seed, parent with a proprietary selection of *Argyranthemum frutescens* identified as code number X01.450.2, as the male, or pollen, parent. The new *Argyranthemum* was discovered and selected by the Inventor as a single flowering plant within the progeny of the stated open-pollination in a controlled environment Cobbitty, New South Wales, Australia in December, 2003.

Asexual reproduction of the new *Argyranthemum* by vegetative tip cuttings in a controlled environment in Cobbitty, New South Wales, Australia has shown that the unique features of this new *Argyranthemum* are stable and reproduced true to type in successive generations.

SUMMARY OF THE INVENTION

Plants of the cultivar Supa742 have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Supa742'. These characteristics in combination distinguish 'Supa742' as a new and distinct potted *Argyranthemum* cultivar:

1. Compact, uniform, outwardly spreading and mounded plant habit.
2. Freely branching growth habit.
3. Freely flowering habit.
4. Daisy-type inflorescences with red purple-colored ray florets.
5. Good garden performance.

Plants of the new *Argyranthemum* differ from plants of the female parent selection primarily in ray floret color as plants of the female parent selection have pink-colored ray florets. Plants of the new *Argyranthemum* differ from plants of the male parent selection primarily in ray floret color as plants of the male parent selection have dark pink-colored ray florets.

Plants of the new *Argyranthemum* can be compared to plants of the *Argyranthemum* cultivar Supalight, disclosed in U.S. Plant Pat. No. 14,128. In side-by-side comparisons conducted in Cobbitty, New South Wales, Australia, plants of the new *Argyranthemum* differed from plants of the cultivar Supalight in the following characteristics:

1. Plants of the new *Argyranthemum* were more compact than plants of the cultivar Supalight.
2. Plants of the new *Argyranthemum* and the cultivar Supalight differed in ray floret coloration as plants of the cultivar Supalight had dark pink-colored ray florets.

BRIEF DESCRIPTION OF THE PHOTOGRAPHS

The accompanying photographs illustrate the overall appearance of the new *Argyranthemum.* These photographs show the colors as true as it is reasonably possible to obtain in colored reproductions of this type. Colors in the photographs may differ slightly from the color values cited in the detailed botanical description which accurately describe the colors of the new *Argyranthemum.*

The photograph on at the bottom of the sheet comprises a side perspective view of a typical flowering plant of 'Supa742'.

The photograph at the top of the sheet is a close-up view of typical inflorescences of 'Supa742'.

DETAILED BOTANICAL DESCRIPTION

The aforementioned photographs and following observations and measurements describe plants grown during the late winter and early spring in Encinitas, Calif. and under conditions and practices which approximate those generally used in commercial potted *Argyranthemum* production. Plants were initially grown in a polyethylene-covered greenhouse and then grown for the last two months in an outdoor nursery. During the production of the plants, day temperatures averaged 24° C. and night temperatures averaged 19° C. Plants were pinched about six weeks after planting. Plants used in the photographs and for the description were about five months old. In the following description, color references are made to The Royal Horticultural Society Colour Chart, 1995 Edition, except where general terms of ordinary dictionary significance are used.

Botanical classification: *Argyranthemum frutescens* cultivar Supa742.

Parentage:

*Female, or seed, parent.*—Proprietary selection of *Argyranthemum frutescens* identified as code number X01.329.2, not patented.

*Male, or pollen, parent.*—Proprietary selection of *Argyranthemum frutescens* identified as code number X01.450.2, not patented.

Propagation:

*Type.*—Terminal cuttings.

*Time to initiate roots.*—About ten days at temperatures of about 20° C.

*Time to produce a rooted young plant.*—About three weeks at temperatures of about 20° C.

*Root description.*—Fine, fibrous; white in color.

*Rooting habit.*—Freely branching; dense.

Plant description:

*Appearance.*—Herbaceous daisy-type potted *Argyranthemum.* Compact, uniform, outwardly spreading and mounded plant habit. Strong and freely branching growth habit with lateral branches potentially developing at every node; dense and full plants. Vigorous growth habit.

*Plant height.*—About 22 cm.

*Plant width.*—About 38 cm.

*Lateral branches.*—Length: About 21 cm. Diameter: About 5 mm. Internode length: About 1.2 cm. Strength: Strong; young stems, flexible. Texture: Young stems, smooth, glabrous; older stems, woody. Color, young stems: 146D. Color, older stems: 200D.

Foliage description:

*Arrangement.*—Alternate, simple.

*Length.*—About 3 cm.

*Width.*—About 2.1 cm.

*Shape.*—Deeply dissected with five to seven lobes.

*Apex.*—Acute.

*Base.*—Attenuate.

*Margin.*—Pinnatifid; entire.

*Texture, upper and lower surfaces.*—Smooth, glabrous.

*Venation pattern.*—Pinnate.

*Color.*—Developing foliage, upper and lower surfaces: 147A. Fully expanded foliage, upper surface: 147A; venation, 147B. Fully expanded foliage, lower surface: 137A; venation, 137B.

*Petiole length.*—About 1.2 cm.

*Petiole diameter.*—About 2 mm.

*Petiole texture, upper and lower surfaces.*—Smooth, glabrous.

*Petiole color, upper surface.*—146B.

*Petiole color, lower surface.*—137B.

Inflorescence description:

*Appearance.*—Daisy-type inflorescence form with ligulate-shaped ray florets. Inflorescences borne on terminals above foliage. Disk and ray florets arranged acropetally on a capitulum. Inflorescences not fragrant.

*Flowering season.*—Plants flower from spring to early fall in Southern California; flowering continuous during this period.

*Inflorescence longevity.*—Inflorescences last about ten days on the plant; inflorescences persistent.

*Quantity of inflorescences.*—Freely flowering, about 225 inflorescences develop per plant.

*Inflorescence bud.*—Height: About 1 cm. Diameter: About 8 mm. Shape: Ovoid. Color: 77B.

*Inflorescence size.*—Diameter: About 3.4 cm. Depth (height): About 9 mm. Diameter of disc: About 1.3 cm. Receptacle height: About 7 mm. Receptacle diameter: About 1.5 cm.

*Ray florets.*—Shape: Ligulate. Orientation: Initially upright, then about 90° from vertical or perpendicular to peduncle; slightly reflexing. Length: About 1.4 cm. Width: About 5 mm. Apex: Emarginate. Base: Acute. Margin: Entire. Texture, upper and lower surfaces: Smooth, glabrous, satiny. Number of ray florets per inflorescence: About 22 arranged in a single whorl. Color: When opening, upper surface: More red than 59A. When opening, lower surface: 71C. Fully opened, upper surface: Slightly darker than 61A; towards the base, 155A. With development, color becoming closer to 77C progressing to 75D and eventually becoming nearly white. Fully opened, lower surface: 70C.

*Disc florets.*—Arrangement: Massed at center of receptacle. Shape: Tubular, elongated. Apex: Five-pointed. Length: About 6 mm. Width, at apex: About 1.5 mm. Width, at base: About 1 mm. Number of disc florets per inflorescence: About 140. Color: Immature: 185A. Mature: Apex: 17C. Mid-section: 145C. Base: 145D.

*Phyllaries.*—Number of phyllaries per inflorescence: About 36 in three or four whorls. Length: About 4 mm. Width: About 2 mm. Shape: Elliptical. Apex: Acute. Base: Truncate. Margin: Entire. Texture, upper and lower surfaces: Smooth, glabrous. Color, upper surface: 145A. Color, lower surface: 146A.

*Peduncles.*—Length, terminal peduncle: About 10.2 cm. Length, second peduncle: About 10.5 cm. Length, fourth peduncle: About 11.2 cm. Diameter: About 1 mm. Angle: Erect to about 35° to 45° from vertical. Strength: Strong, flexible. Texture: Smooth, glabrous. Color: 146B.

*Reproductive organs.*—Androecium: Present on disc florets only. Anther length: About 2 mm. Anther shape: Oblong. Anther color: 13A. Pollen amount: Scarce. Pollen color: 13A. Gynoecium: Present on both ray and disc florets. Pistil length: About 4 mm. Stigma shape: Two-parted. Stigma color: 7A. Style length: About 2 mm. Style color: 145C. Ovary color: 145C.

*Seed/fruit.*—Seed and fruit production has not been observed.

Disease/pest resistance: Resistance to pathogens and pests common to *Argyranthemums* has not been observed on plants grown under commercial conditions.

Garden performance: Plants of the new *Argyranthemum* have been observed to have good garden performance and to tolerate wind, rain and temperatures from about −1° C. to about 30° C.

It is claimed:

1. A new and distinct *Argyranthemum* plant named 'Supa742' as illustrated and described.

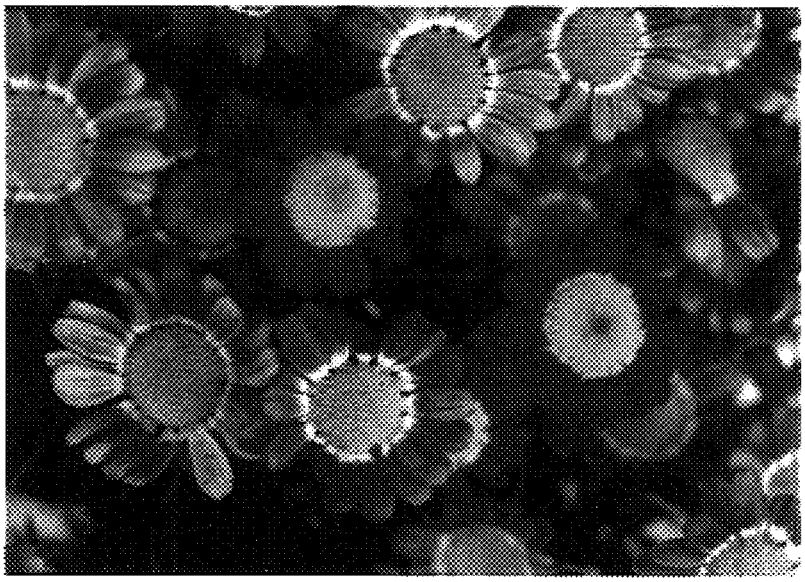
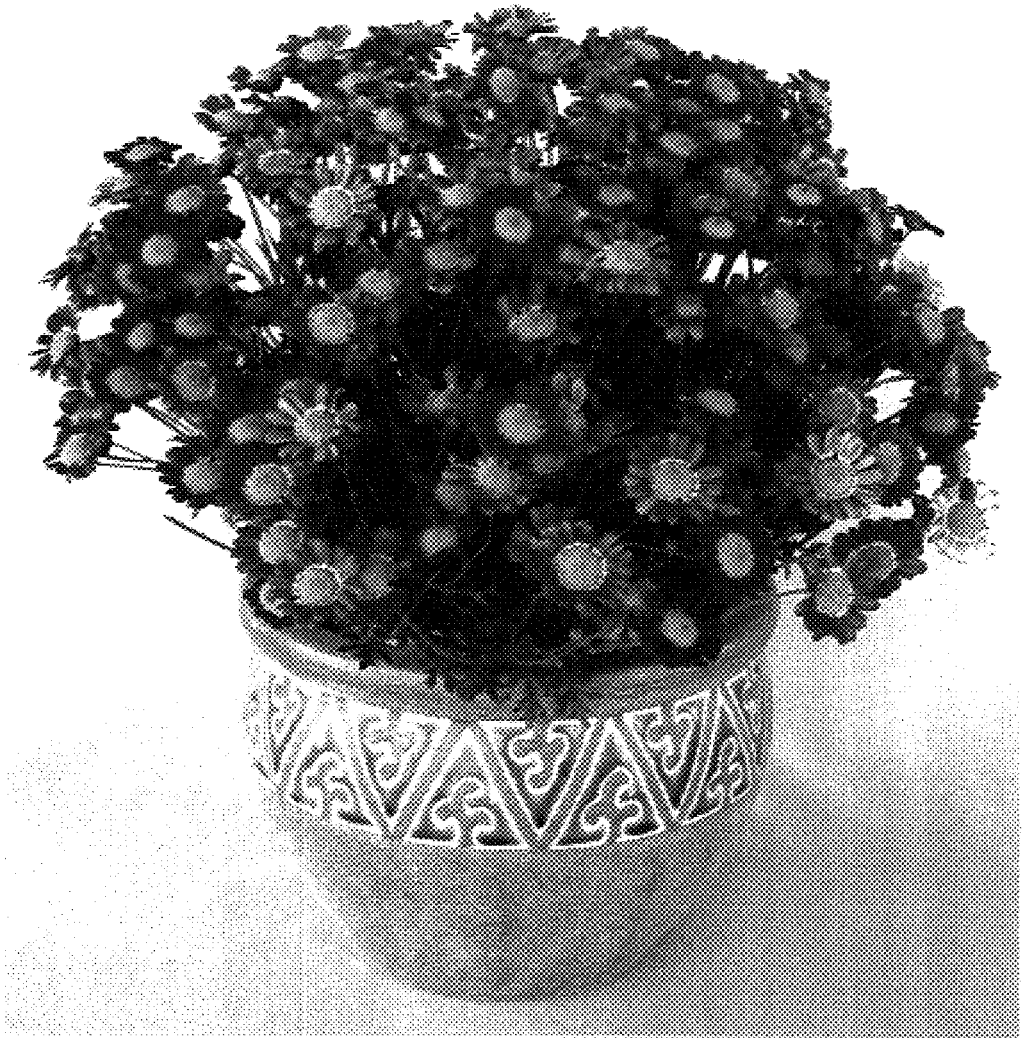

* * * * *